(12) United States Patent
Ni et al.

(10) Patent No.: US 11,078,465 B2
(45) Date of Patent: Aug. 3, 2021

(54) ALCOHOL DEHYDROGENASE MUTANT AND APPLICATION THEREOF IN SYNTHESIS OF DIARYL CHIRAL ALCOHOLS

(71) Applicant: Jiangnan University, Wuxi (CN)

(72) Inventors: Ye Ni, Wuxi (CN); Yue Wang, Wuxi (CN); Wei Dai, Wuxi (CN); Guochao Xu, Wuxi (CN); Jieyu Zhou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/521,067

(22) Filed: Jul. 24, 2019

(65) Prior Publication Data

US 2019/0345455 A1    Nov. 14, 2019

Related U.S. Application Data

(63) Continuation of application No. PCT/CN2018/094507, filed on Jul. 4, 2018.

(30) Foreign Application Priority Data

Feb. 12, 2018  (CN) .......................... 201810145970.9

(51) Int. Cl.
  *C12N 9/04*  (2006.01)
  *C12P 17/12*  (2006.01)
(52) U.S. Cl.
  CPC ............ *C12N 9/0006* (2013.01); *C12P 17/12* (2013.01); *C12Y 101/01001* (2013.01)
(58) Field of Classification Search
  CPC ...... C12N 9/0006; C12P 17/12; C12P 41/002; C12Y 101/01001
  See application file for complete search history.

(56) References Cited

U.S. PATENT DOCUMENTS 10,865,390 B2 * 12/2020 Ni ........................... C12P 17/12

FOREIGN PATENT DOCUMENTS

| CN | 103642765 A | 3/2014 |
|----|-------------|--------|
| CN | 104531628 A | 4/2015 |
| CN | 105936895 A | 9/2016 |
| CN | 105936909 A | 9/2016 |

OTHER PUBLICATIONS

PIR/UniProt Accession No. F86228, created Mar. 2, 2001.*
Whisstock et al. Quaterly Reviews of Biophysics, 2003, "Prediction of protein function from protein sequence and structure", 36(3): 307-340.*
Chica et al., Semi-rational approaches to engineering enzyme activity: combining the benefits of directed evolution and rational design. Curr. Opi. Biotechnol., 2005, vol. 16: 378-384.*
Witkowski et al. Conversion of a beta-ketoacyl synthase to a malonyl decarboxylase by replacement of the active-site cysteine with glutamine, Biochemistry. Sep. 7, 1999;38(36): 11643-50.*

* cited by examiner

*Primary Examiner* — Iqbal H Chowdhury
(74) *Attorney, Agent, or Firm* — IPro, PLLC

(57) ABSTRACT

The present disclosure discloses an alcohol dehydrogenase mutant and application thereof in synthesis of diaryl chiral alcohols, and belongs to the technical field of bioengineering. The alcohol dehydrogenase mutant of the present disclosure has excellent catalytic activity and stereoselectivity, and may efficiently catalyze the preparation of a series of chiral diaryl alcohols in R- and S-configurations. By coupling alcohol dehydrogenase of the present disclosure to glucose dehydrogenase or formate dehydrogenase, the synthesis of chiral diaryl alcohol intermediates of various antihistamines may be achieved. Compared with the prior art, a method for preparing diaryl chiral alcohols through asymmetric catalytic reduction using the alcohol dehydrogenase of the present disclosure has the advantages of simple and convenient operation, high substrate concentration, complete reaction and high product purity, and has great industrial application prospects.

2 Claims, 4 Drawing Sheets

Specification includes a Sequence Listing.

```
                        SEQUENCE LISTING

<160> NUMBER OF SEQ ID NOS: 44

<210> SEQ ID NO 1
<211> LENGTH: 1029
<212> TYPE: DNA
<213> ORGANISM: Artificial Sequence
<220> FEATURE:
<223> OTHER INFORMATION: Synthetic DNA

<400> SEQUENCE: 1
atgagcgtat taattagtgg tgcttctgga tacattgcca acatatcgt cagagttctt      60 ttggaacaaa attacaaagt aattggtact gttagaagtc aagacaaagc tgataagtta     120
ttgaaacaat ataataatcc taatttgtct tatgaaattg tacctgaaat agcaaactta     180
gatgcttttg atgacatttt taagaaacat ggtaaggaaa taaatatgt cattcatgca     240 gcttcaccag tgaacttcgg cgcaaaagat ttggaaaaag atttagttat tcctgccatt     300
aatggtacca agaatatgtt cgaagctatt aaaaagtatg ccccagatac tgtcgaacgt     360
```

-continued

```
gttgtaatga ctgcttctta tgcttcaatt atgaccccac atagacaaaa tgatccaact    420
ttaactttag atgaagaaac ttggaatcca gtaactgaag aaaatgctta tgaaaatgtc    480
ttcactgctt attgtgcttc aaaaactttt gctgaaaagg aagcttggaa gttcgttaaa    540
gaaaatagtg atgctgttaa gtttaaacta accactatcc acccatcctt cgttttcgga    600
cctcagaact ttgatgaaga cgtcactaag aaactaaatg aaacttgtga aattatcaat    660
ggtttattac atgctccatt tgacaccaaa gtcgaaaaga ctcacttcag tcaattcatt    720
gatgttcgtg atgtcgccaa aactcacgtt ttgggtttcc aaaaagatga attaatcaac    780
caaagattgt tattatgtaa cggcgccttc tctcaacaag atattgttaa tgtatttaat    840
gaagatttcc cagagttaaa aggccaattc ccaccagaag ataaggacac cgatttaaac    900
aaaggtgtaa caggttgtaa aattgataat gaaaagacta aaaaattatt agcatttgaa    960
tttactcctt tccataaaac aattcatgac actgtctatc aaattttaca taaagaaggt   1020
agagtttaa                                                           1029
```

```
<210> SEQ ID NO 2
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 2
```

```
Met Ser Val Leu Ile Ser Gly Ala Ser Gly Tyr Ile Ala Lys His Ile
 1               5                  10                  15

Val Arg Val Leu Leu Glu Gln Asn Tyr Lys Val Ile Gly Thr Val Arg
             20                  25                  30

Ser Gln Asp Lys Ala Asp Lys Leu Leu Lys Gln Tyr Asn Asn Pro Asn
         35                  40                  45

Leu Ser Tyr Glu Ile Val Pro Glu Ile Ala Asn Leu Asp Ala Phe Asp
     50                  55                  60

Asp Ile Phe Lys Lys His Gly Lys Glu Ile Lys Tyr Val Ile His Ala
 65                  70                  75                  80

Ala Ser Pro Val Asn Phe Gly Ala Lys Asp Leu Glu Lys Asp Leu Val
                 85                  90                  95

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Tyr Ala
        115                 120                 125

Ser Ile Met Thr Pro His Arg Gln Asn Asp Pro Thr Leu Thr Leu Asp
    130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
            180                 185                 190

Ile His Pro Ser Phe Val Phe Gly Pro Gln Asn Phe Asp Glu Asp Val
        195                 200                 205

Thr Lys Lys Leu Asn Glu Thr Cys Glu Ile Ile Asn Gly Leu Leu His
    210                 215                 220

Ala Pro Phe Asp Thr Lys Val Glu Lys Thr His Phe Ser Gln Phe Ile
225                 230                 235                 240
```

-continued

Asp Val Arg Asp Val Ala Lys Thr His Val Leu Gly Phe Gln Lys Asp
                245                 250                 255

Glu Leu Ile Asn Gln Arg Leu Leu Leu Cys Asn Gly Ala Phe Ser Gln
            260                 265                 270

Gln Asp Ile Val Asn Val Phe Asn Glu Asp Phe Pro Glu Leu Lys Gly
        275                 280                 285

Gln Phe Pro Pro Glu Asp Lys Asp Thr Asp Leu Asn Lys Gly Val Thr
    290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
agaaactaaa tgcaacttgt g                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
tcacaagttg catttagttt c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
agaaactaaa taccacttgt g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
tcacaagtgg aatttagttt c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

```
<400> SEQUENCE: 7
agaaactaaa tgcaacttgt g                                      21

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA

<400> SEQUENCE: 8
tcacaagttg catttagttt c                                      21

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
agaaactaaa taatacttgt g                                      21

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
tcacaagtat tatttagttt c                                      21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
agaaactaaa tgatacttgt g                                      21

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
tcacaagtat catttagttt c                                      21

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
agaaactaaa ttgtacttgt g                                      21
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
tcacaagtac aatttagttt c                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
agaaactaaa tgaaacttgt g                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
tcacaagttt catttagttt c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic DNA

<400> SEQUENCE: 17
agaaactaaa tcagacttgt g                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA

<400> SEQUENCE: 18
tcacaagtct gatttagttt c                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA

<400> SEQUENCE: 19
agaaactaaa tggtacttgt g                                              21

<210> SEQ ID NO 20
<211> LENGTH: 21
<212> TYPE: DNA
<213> ORGANISM: Artificial Sequence
<220> FEATURE:
```

<223> OTHER INFORMATION: Synthetic DNA

<400> SEQUENCE: 20
tcacaagtcc aatttagttt c                                        21

<210> SEQ ID NO 21
<211> LENGTH: 21
<212> TYPE: DNA
<213> ORGANISM: Artificial Sequence
<220> FEATURE:
<223> OTHER INFORMATION: Synthetic DNA

<400> SEQUENCE: 21
agaaactaaa tcatacttgt g                                        21

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA

<400> SEQUENCE: 22
tcacaagtat gatttagttt c                                        21

<210> SEQ ID NO 23
<211> LENGTH: 21
<212> TYPE: DNA
<213> ORGANISM: Artificial Sequence
<220> FEATURE:
<223> OTHER INFORMATION: Synthetic DNA

<400> SEQUENCE: 23
agaaactaaa tattacttgt g                                        21

<210> SEQ ID NO 24
<211> LENGTH: 21
<212> TYPE: DNA
<213> ORGANISM: Artificial Sequence
<220> FEATURE:
<223> OTHER INFORMATION: Synthetic DNA

<400> SEQUENCE: 24
tcacaagtaa tatttagttt c                                        21

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA

<400> SEQUENCE: 25
agaaactaaa tctgacttgt g                                        21

<210> SEQ ID NO 26
<211> LENGTH: 21
<212> TYPE: DNA
<213> ORGANISM: Artificial Sequence
<220> FEATURE:
<223> OTHER INFORMATION: Synthetic DNA

<400> SEQUENCE: 26
tcacaagtca gatttagttt c                                        21

```
<210> SEQ ID NO 27
<211> LENGTH: 21
<212> TYPE: DNA
<213> ORGANISM: Artificial Sequence
<220> FEATURE:
<223> OTHER INFORMATION: Synthetic DNA

<400> SEQUENCE: 27
agaaactaaa taaaacttgt g                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic DNA

<400> SEQUENCE: 28
tcacaagttt tatttagttt c                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic DNA

<400> SEQUENCE: 29
agaaactaaa tatgacttgt g                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic DNA

<400> SEQUENCE: 30
tcacaagtca tatttagttt c                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic DNA

<400> SEQUENCE: 31
agaaactaaa ttttacttgt g                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic DNA

<400> SEQUENCE: 32
tcacaagtaa aatttagttt c                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic DNA
```

```
<400> SEQUENCE: 33
agaaactaaa tccgacttgt g                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic DNA

<400> SEQUENCE: 34
tcacaagtcg gatttagttt c                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic DNA

<400> SEQUENCE: 35
agaaactaaa ttggacttgt g                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic DNA

<400> SEQUENCE: 36
tcacaagtcc tatttagttt c                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic DNA

<400> SEQUENCE: 37
agaaactaaa ttatacttgt g                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic DNA

<400> SEQUENCE: 38
tcacaagtat aatttagttt c                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic DNA

<400> SEQUENCE: 39
agaaactaaa tgttacttgt g                                              21

<210> SEQ ID NO 40
<211> LENGTH: 21
```

```
<212> TYPE: DNA
<213> ORGANISM: Artificial Sequence
<220> FEATURE:
<223> OTHER INFORMATION: Synthetic DNA

<400> SEQUENCE: 40
tcacaagtaa catttagttt c                                          21

<210> SEQ ID NO 41
<211> LENGTH: 21
<212> TYPE: DNA
<213> ORGANISM: Artificial Sequence
<220> FEATURE:
<223> OTHER INFORMATION: Synthetic DNA

<400> SEQUENCE: 41
actcacttcg cacaattcat t                                          21

<210> SEQ ID NO 42
<211> LENGTH: 21
<212> TYPE: DNA
<213> ORGANISM: Artificial Sequence
<220> FEATURE:
<223> OTHER INFORMATION: Synthetic DNA

<400> SEQUENCE: 42
aatgaattgt gcgaagtgag t                                          21

<210> SEQ ID NO 43
<211> LENGTH: 21
<212> TYPE: DNA
<213> ORGANISM: Artificial Sequence
<220> FEATURE:
<223> OTHER INFORMATION: Synthetic DNA

<400> SEQUENCE: 43
actcacttct gtcaattcat t                                          21

<210> SEQ ID NO 44
<211> LENGTH: 21
<212> TYPE: DNA
<213> ORGANISM: Artificial Sequence
<220> FEATURE:
<223> OTHER INFORMATION: Synthetic DNA

<400> SEQUENCE: 44
aatgaattga cagaagtgag t                                          21
```

ALCOHOL DEHYDROGENASE MUTANT AND APPLICATION THEREOF IN SYNTHESIS OF DIARYL CHIRAL ALCOHOLS

TECHNICAL FIELD

The present disclosure relates to an alcohol dehydrogenase mutant and application thereof in synthesis of diaryl chiral alcohols, and belongs to the technical field of bioengineering.

BACKGROUND

Chiral diaryl alcohol compounds are key chiral intermediates for the synthesis of numerous drugs and fine chemicals, where chiral (4-chlorophenyl)-(pyridin-2-yl)-methanol (CPMA) is a key chiral intermediate for the synthesis of an antihistamine drug betahistine. The synthesis of chiral CPMA by chemical asymmetric reduction using prochiral (4-chlorophenyl)-(pyridin-2-yl)-methanone (CPMK) as a raw material is mainly achieved by the following five techniques:

1. at a substrate concentration of 1.0 mM, using trans-$RuCl_2[(R)$-xylbinap$][(R)$-daipen$]$ as a catalyst to react at room temperature for 24 h under the nitrogen pressure of 40-60 psi, so as to obtain (S)-(4-chlorophenyl)-(pyridin-2-yl)-methanol ((S)-CPMA) with an ee value of 60.6% and a yield of 98% through reduction (C. Y. Chen, et al., *Org. Lett.*, 2003, 5, 5039-5042);

2. using (S)—[Ru(BINAP)$Cl_2]_2(NE_3)$ as a catalyst to obtain (S)—CPMA with an ee value of 99% through pressurization, hydrogenation and reduction (Zhao Zhiquan, et al., Chinese Journal of Pharmaceuticals, 2006, 37, 726-727);

3. using CPMK as a raw material and (S,S)-6-CHOONa as a catalyst to react at 50° C. and a substrate concentration of only 0.2 mM for 24 h, so as to obtain (R)-(4-chlorphenyl)-(pyridin-2-yl)-methanol ((R)-CPMA) with an ee value of 40.8% and a yield of 90% through reduction (B. G. Wang, *Org. Lett.*, 2017, 19, 2094-2097);

4. using CPMK as a raw material for three-step reaction, (1) first protecting with trifluoromethanesulfonic anhydride and the like, (2) using a catalyst palladium ligand and Me-CBS to reduce a carbonyl group to an S configuration hydroxyl group, and (3) performing deprotection by triphenylphosphine palladium, so as to obtain (S)-CPMA (Chinese patent CN101848893A); and 5. using chiral BINAL-H as a chiral reducing agent for oriented synthesis of a single configuration of CPMA at a substrate concentration of 400 mM CMPK, where after recrystallization of ethyl acetate-petroleum ether, the yield of (R)-CPMA is 88.2%, the purity is 96.2%, the yield of (S)-CPMA is 87.4%, and the purity is 95.7% (Chinese patent CN103122376A).

It can be seen that the above reactions have the problems of high cost of the noble metal ligand catalysts, low substrate concentration, high pressure conditions for the reactions, many operation steps, and low optical purity of the materials, which cannot meet the requirements of drugs on the optical purity, and is not favorable for industrial production.

Biocatalysis refers to a process of chemical conversion using enzymes or biological organisms (cells, organelles, tissues, etc.) as a catalyst under mild action conditions, which is completed in an environment of normal temperature, a neutral environment, water or the like, and has unique advantages for the synthesis of chiral active pharmaceutical ingredients. It meets the goals of industrial development such as "sustainable development", "green chemistry" and "environmentally benign manufacturing". Compared with chemical synthesis methods, the use of alcohol dehydrogenase to asymmetrically reduce the carbonyl group in prochiral ketone has the advantages of high stereoselectivity, mild reaction conditions and the like, and has important economic and social values and ecological significance. The biological asymmetric reduction method may be realized mainly by the following four techniques:

1. in 2007, after Truppo et al. screened a series of commercial ketoreductases KRED, it was found that although some ketoreductases had a reducing ability to diaryl substrates, the stereoselectivity was just ordinary, a substrate spectrum was narrow, and substituent groups in the substrates had a great impact on the stereoselectivity; and only KRED124 may asymmetrically reduce CPMK to generate (R)-CPMA, the ee value was 94%, the conversion rate was 98%, and the addition of glucose dehydrogenase was required to achieve coenzyme circulation (M. D. Truppo, *Org. Lett.*, 2007, 9, 335-338);

2. in 2009, Zhu Dunming et al. discovered that a recombinant carbonyl reductase SsCR derived from *Sporobolomyces salmonicolor* and mutants thereof may stereoselectively reduce different diaryl ketone substrates (8-99% ee), with the aid of glucose dehydrogenase, (R)-CPMA was generated by reducing CPMK, the conversion rate was 62%, and the enantioselectivity was 88% (R) (D. M. Zhu, *Org. Lett.*, 2008, 10, 525-528);

3. in 2012, Zhou Jieyu et al. screened a *Kluyveromyces* sp. CCTCCM2011385 by traditional enrichment culture, which may catalyze the reduction of CPMK to generate (S)-CPMA (87% ee), however, due to the low content of active enzyme in wild fungi, only a 2 g/L substrate may be catalyzed at most, the product concentration is low, and the separation cost is high, so it cannot meet application needs, (Y. Ni, *Process Biochem.*, 2012, 47, 1042-1048; Chinese patent CN102559520A); and 4. in 2013, Li Zhe et al. studied the asymmetric reduction to a series of diaryl ketones by a carbonyl reductase PasCR derived from *Pichia pastoris* GS115, the substrate concentration was 10 mM and the conversion rate was only 50% at most, (Li Zhe, et al., *Chinese Journal of Biotechnology*, 2013, 29, 68-77).

It can be seen that the stereoselectivity for preparing chiral CPMA by the biological asymmetric reduction method can hardly meet the pharmaceutical requirement for an enantiomeric excess of more than 95%, and in particular, a reductase for synthesizing and preparing (S)-CPMA is unavailable, so there is an urgent need to develop a highly efficient and highly stereoselective bioenzyme catalyst.

SUMMARY

In view of the problem of low stereoselectivity of alcohol dehydrogenase in the prior art, the present disclosure provides a series of alcohol dehydrogenase mutant proteins, a nucleic acid sequence encoding the mutant proteins, a recombinant expression vector and a recombinant expression transformant containing the nucleic acid sequence, and the application of the alcohol dehydrogenase mutant proteins or the recombinant transformant expressing the alcohol dehydrogenase mutant proteins as a catalyst in asymmetric reduction and preparation of an optical chiral diaryl alcohol.

The present disclosure provides an alcohol dehydrogenase mutant with higher reactivity and stereoselectivity.

In an embodiment of the present disclosure, the amino acid sequence of the alcohol dehydrogenase mutant includes an amino acid sequence obtained by mutation of one or two amino acid sites of amino acid glutamate at position 214 and amino acid serine at position 237 in an amino acid sequence shown in SEQ ID No. 2.

In an embodiment of the present disclosure, the mutant includes the substitution of valine for glutamate at position 214 of the alcohol dehydrogenase with the amino acid sequence shown in SEQ ID No. 2 (E214V), which is named M1.

In an embodiment of the present disclosure, the mutant includes the substitution of tyrosine for glutamate at position 214 of the alcohol dehydrogenase with the amino acid sequence shown in SEQ ID No. 2 (E214Y), which is named M2.

In an embodiment of the present disclosure, the mutant includes the substitution of isoleucine for glutamate at position 214 of the alcohol dehydrogenase with the amino acid sequence shown in SEQ ID No. 2 (E214I), which is named M3.

In an embodiment of the present disclosure, the mutant includes the substitution of glycine for glutamate at position 214 of the alcohol dehydrogenase with the amino acid sequence shown in SEQ ID No. 2 (E214G), which is named M4.

In an embodiment of the present disclosure, the mutant includes the substitution of glutamine for glutamate at position 214 of the alcohol dehydrogenase with the amino acid sequence shown in SEQ ID No. 2 (E214Q), which is named M5.

In an embodiment of the present disclosure, the mutant includes the substitution of serine for glutamate at position 214 of the alcohol dehydrogenase with the amino acid sequence shown in SEQ ID No. 2 (E214S), which is named M6.

In an embodiment of the present disclosure, the mutant includes the substitution of asparagine for glutamate at position 214 of the alcohol dehydrogenase with the amino acid sequence shown in SEQ ID No. 2 (E214N), which is named M7.

In an embodiment of the present disclosure, the mutant includes the substitution of arginine for glutamate at position 214 of the alcohol dehydrogenase with the amino acid sequence shown in SEQ ID No. 2 (E214R), which is named M8.

In an embodiment of the present disclosure, the mutant includes the substitution of valine for glutamate at position 214 of the alcohol dehydrogenase with the amino acid sequence shown in SEQ ID No. 2, and the substitution of alanine for serine at position 237 (E214V/S237A), which is named M9.

In an embodiment of the present disclosure, the mutant includes the substitution of tyrosine for glutamate at position 214 of the alcohol dehydrogenase with the amino acid sequence shown in SEQ ID No. 2, and the substitution of alanine for serine at position 237 (E214Y/S237A), which is named M10.

In an embodiment of the present disclosure, the mutant includes the substitution of isoleucine for glutamate at position 214 of the alcohol dehydrogenase with the amino acid sequence shown in SEQ ID No. 2, and the substitution of alanine for serine at position 237 (E214I/S237A), which is named M11.

In an embodiment of the present disclosure, the mutant includes the substitution of glycine for glutamate at position 214 of the alcohol dehydrogenase with the amino acid sequence shown in SEQ ID No. 2, and the substitution of cysteine for serine at position 237 (E214G/S237C), which is named M12.

In an embodiment of the present disclosure, the mutant includes the substitution of glutamine for glutamate at position 214 of the alcohol dehydrogenase with the amino acid sequence shown in SEQ ID No. 2, and the substitution of cysteine for serine at position 237 (E214Q/S237C), which is named M13.

In an embodiment of the present disclosure, the mutant includes the substitution of serine for glutamate at position 214 of the alcohol dehydrogenase with the amino acid sequence shown in SEQ ID No. 2, and the substitution of cysteine for serine at position 237 (E214S/S237C), which is named M14.

In an embodiment of the present disclosure, the mutant includes the substitution of asparagine for glutamate at position 214 of the alcohol dehydrogenase with the amino acid sequence shown in SEQ ID No. 2, and the substitution of cysteine for serine at position 237 (E214N/S237C), which is named M15.

In an embodiment of the present disclosure, the mutant includes the substitution of arginine for glutamate at position 214 of the alcohol dehydrogenase with the amino acid sequence shown in SEQ ID No. 2, and the substitution of cysteine for serine at position 237 (E214R/S237C), which is named M16.

In an embodiment of the present disclosure, the nucleotide sequence of the gene encoding the alcohol dehydrogenase is shown in SEQ ID No. 1.

In an embodiment of the present disclosure, a recombinant strain expressing the mutant is provided.

In an embodiment of the present disclosure, a method for constructing the recombinant strain includes the following steps: cloning a nucleic acid molecule encoding the mutant into a recombinant vector, transforming the resulting recombinant vector into a transformant to obtain a recombinant expression transformant, and culturing the resulting recombinant expression transformant and conducting isolation and purification to obtain the mutant.

In an embodiment of the present disclosure, the host of the recombinant strain is *Escherichia coli*, and plasmid is pET28a (+).

In an embodiment of the present disclosure, the host of the recombinant strain is *E. coli* BL21 (DE3).

The present disclosure also provides a method for producing an alcohol dehydrogenase by using the recombinant strain, specifically including the following steps: inoculating the recombinant strain into an LB medium containing 40-60 μg/mL kanamycin sulfate for shake cultivation at 30-40° C. and 100-200 rpm, adding 0.05-1.0 mM isopropyl-β-D-thiogalactofuranoside (IPTG) for induction at an inducing temperature of 16-30° C. when the absorbance $OD_{600}$ of a medium solution reaches 0.5-1.0, and inducing for 5-10 h to obtain the mutant for efficient expression of the recombinant alcohol dehydrogenase.

In an embodiment of the present disclosure, application of the mutant as a catalyst in the preparation of an optical pure chiral diaryl alcohol by asymmetric reduction of a prochiral carbonyl compound is provided.

In an embodiment of the present disclosure, the prochiral carbonyl compound is (4-chlorophenyl)-(pyridin-2-yl)-methanone (CPMK), phenyl-(pyridin-2-yl)-methanone, (4-chlorophenyl)-(phenyl)-methanone, (4-fluorophenyl)-(phenyl)-methanone, (4-bromophenyl)-(phenyl)-methanone, (4-methoxyphenyl)-(phenyl)-methanone, 1-(pyridin-2-yl)ethanonee, acetophenone, 4'-Chloroacetophenone, 4-Chlorophenacyl Chloride, ethyl 2-oxo-4-phenylbutanoate (OPBE), ethyl 4-chloro-3-oxobutanoate or methyl 2-oxo-2-phenylacetate.

A method for producing chiral CPMA using an alcohol dehydrogenase specifically includes the following steps: constructing a reaction system, where CPMK concentration is 10-500 mM, the amount of the dehydrogenase mutant according to any one of claims 1-3 is 1-10 kU/L, and the amount of NADP$^+$ is 0.1-1.0 mM; adding a coenzyme circulation system, wherein the coenzyme circulation system contains glucose dehydrogenase GDH and D-glucose, the amount of glucose dehydrogenase GDH is 1-10 kU/L, the amount of D-glucose dosage is 20-1000 mM, and the concentration of a phosphate buffer is 0.1-0.2 M; performing reaction at 30-35° C. and pH 6-8 for 1-24 h; and extracting the chiral CPMA from a reaction solution according to an organic solvent extraction method after asymmetric reduction reaction.

In an embodiment of the present disclosure, the coenzyme circulation system may also be phosphite/phosphite dehydrogenase (FTDH), formic acid/formate dehydrogenase (FDH), lactic acid/lactate dehydrogenase (LDH) or glycerol/glycerol dehydrogenase.

In an embodiment of the present disclosure, a chromatographic analysis method is as follows: 100 μL of reactant liquid is taken, 500 μL of ethyl acetate is added, shaking is performed for 1-2 min, centrifugation is performed at 12,000 rpm for 2-5 min, supernatant liquid is taken into a centrifuge tube, after an organic phase naturally volatilizes completely, 500 μL of chromatographically pure ethanol is added, and chiral liquid chromatography and gas chromatography are performed to analyze the transformation rate and the ee value. The conditions of CPMK liquid chromatography are specifically as follows: a Daicel Chiralcel OB-H (5 μm, 250 mm×4.6 mm) liquid chromatographic column is used, the moving phase is n-hexane, ethanol and ethanolamine in ratio of 90:10:0.01 (v/v/v), the flow rate is 0.8 mL/min, the column temperature is 30° C., the ultraviolet detection wavelength is 254 nm, the sample size is 10 μL, and the (S)- and (R)-CPMA retention time is respectively 12.54 min and 13.57 min; the conditions of p-nitrobenzophenone liquid chromatography are specifically as follows: a Daicel Chiralcel OJ-H (5 μm, 250 mm×4.6 mm) liquid chromatographic column is used, the moving phase is n-hexane, isopropanol and ethanolamine in ratio of 90:10:0.01 (v/v/v), the flow rate is 0.8 mL/min, the column temperature is 30° C., the ultraviolet detection wavelength is 254 nm, the sample size is 10 μL, and the (S)- and (R)-retention time is respectively 74.49 min and 95.56 min; the conditions of p-acetophenone gas chromatography are as follows: a CP7502-Chirasil-DEX CB chiral gas column is used, the temperature is maintained at 100° C. for 2 min, the temperature is raised to 180° C. at 4° C./min and maintained for 2 min, the sample size is 2 μL, and the (S)- and (R)-retention time is respectively 10.15 min and 10.85 min; the conditions of p-chloroacetophenone gas chromatography are as follows: a CP7502-Chirasil-DEX CB chiral gas column is used, the temperature is maintained at 100° C. for 2 min, the temperature is raised to 180° C. at 7° C./min and maintained for 2 min, the sample size is 2 μL, and the (S)- and (R)-retention time is respectively 9.26 min and 9.94 min; the conditions of p-chlorobenzoyl chloride gas chromatography are as follows: a CP7502-Chirasil-DEX CB chiral gas column is used, the temperature is maintained at 100° C. for 2 min, the temperature is raised to 180° C. at 5° C./min and maintained for 2 min, the sample size is 2 μL, and the (S)- and (R)-retention time is respectively 16.68 min and 17.55 min.

Beneficial effects of the present disclosure:

(1) the alcohol dehydrogenase mutant obtained in the present disclosure has high activity to various carbonyl compounds, and may catalyze the reduction of a plurality of aliphatic or aryl-substituted ketone substrates, especially diaryl ketone substrates having a large steric hindrance, and molecular modification on KpADH is achieved through the combination of mutation means to increase the stereoselectivity of the enzyme, which will make it more industrially useful;

(2) The positive results of the present invention are as follows: compared with the wild type alcohol dehydrogenase KpADH, the alcohol dehydrogenase single-site mutants E214Y, E214V and E214I of the present invention have higher (R)-CPMA enantioselectivity, the ee thereof is increased from 82% (R) in the wild type to 91% (R), the S237V is increased to 95.3% (R), the enantioselectivity of (R)-CPMA of combined mutants E214V/S237A, E214Y/S237A and E214I/S237A is increased to 97% or above, R type products with an enantiomeric purity greater than 99.9% can be obtained by recrystallization, and have high value. E214G, E214Q, E214S, E214N and E214R have potential of stereoselectivity of reversed (S)-CPMA, the ee is reduced from 82% (R) in wild type to 60% (R) or lower, among which the E214G single-site mutation achieves inversion from an R configuration to an S configuration, the combined mutants E214G/S237C, E214Q/S237C, E214S/S237C, E214N/S237C and E214R/S237C all realize inversion from the R configuration to the S configuration, and these mutational sites are important reference sites for future research. The alcohol dehydrogenase mutants obtained by the present invention are particularly suitable for asymmetric reduction of diaryl ketone, and have good industrial application prospects.

DETAILED DESCRIPTION

Figure 1:
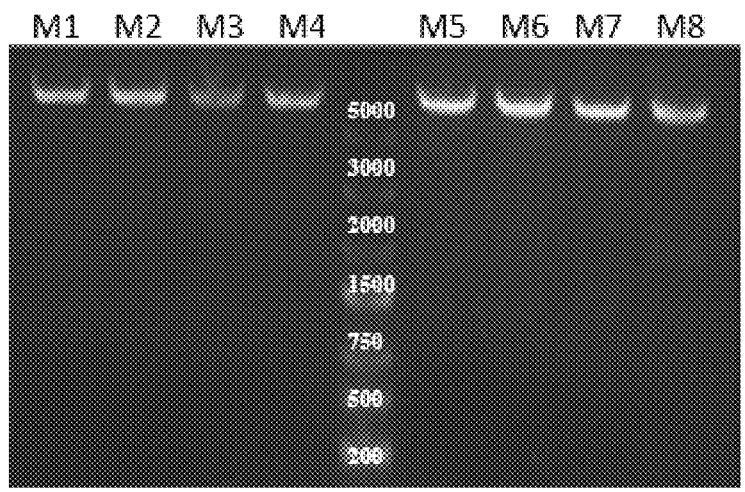
FIG. 1 is whole-plasmid PCR nucleic acid electrophoretograms of alcohol dehydrogenase mutants M1 to M8.
Figure 2:
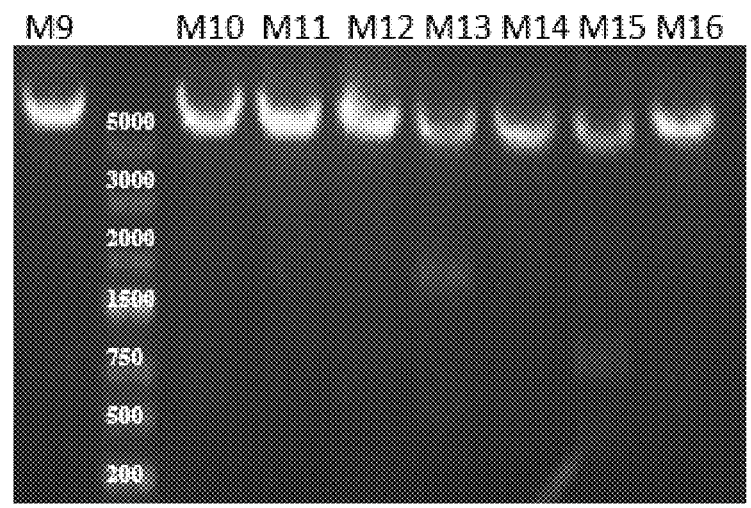
FIG. 2 is whole-plasmid PCR nucleic acid electrophoretograms of alcohol dehydrogenase mutants M9 to M16.
Figure 3:
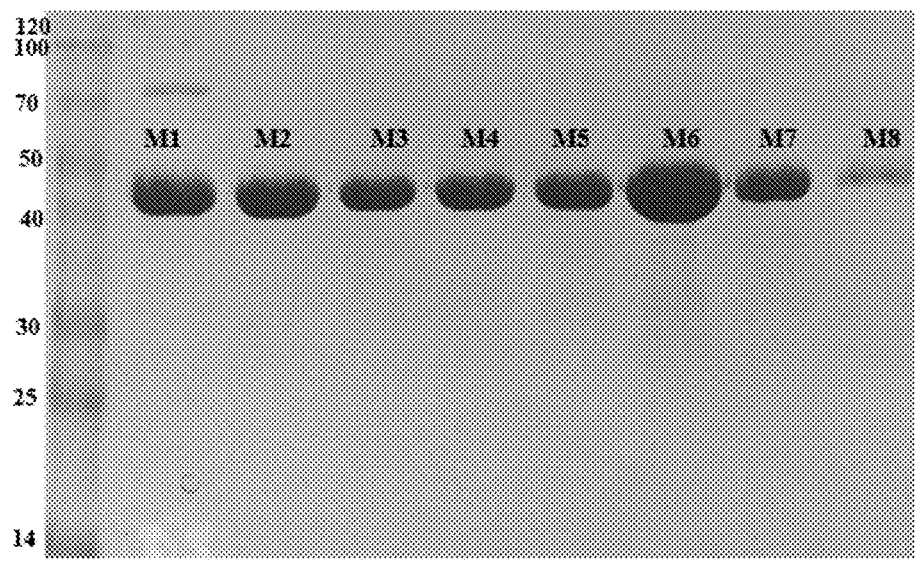
FIG. 3 is SDS-PAGE analysis of alcohol dehydrogenase mutants M1 to M8, respectively.
Figure 4:
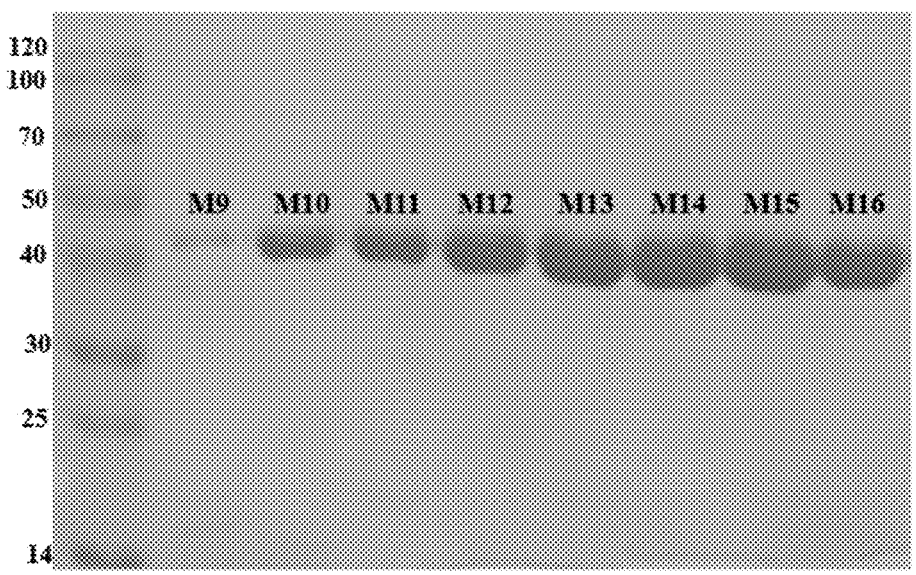
FIG. 4 is SDS-PAGE analysis of alcohol dehydrogenase mutants M9 to M16, respectively.
Figure 5:
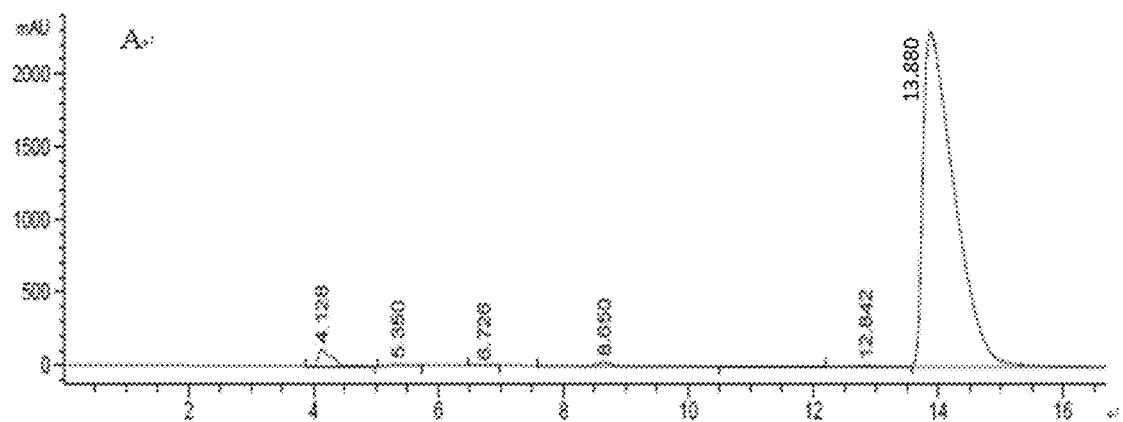
FIG. 5 is a chiral liquid chromatogram of product produced from CPMK reduction catalyzed by an alcohol dehydrogenase mutant M10.
Figure 6:
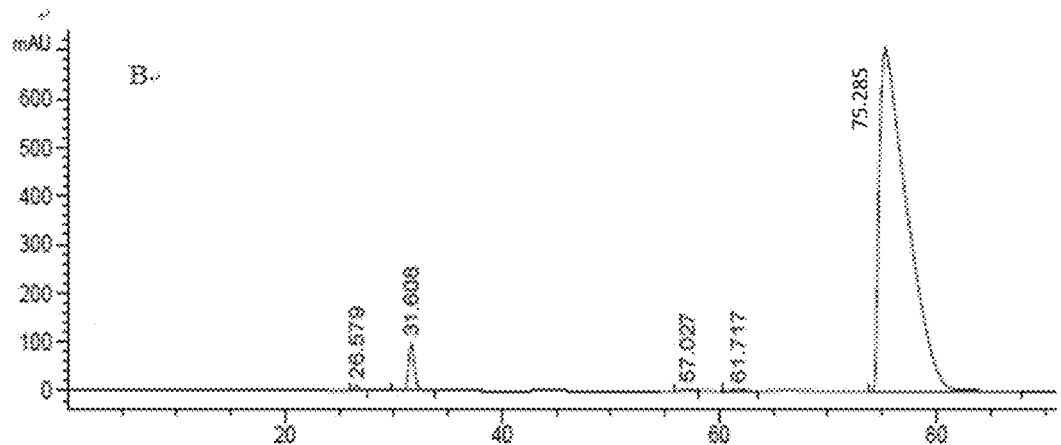
FIG. 6 is a chiral liquid chromatogram of product produced from p-nitrobenzophenone reduction catalyzed by an alcohol dehydrogenase mutant M10.
Figure 7:
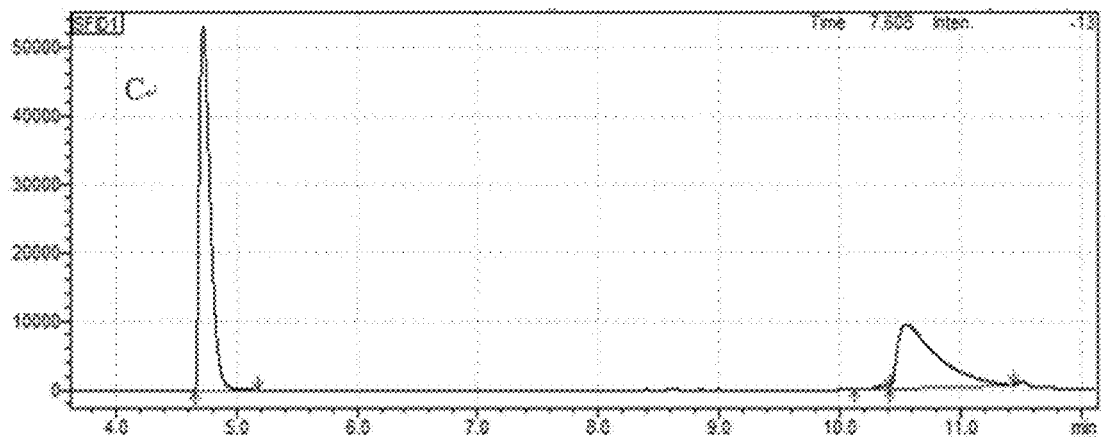
FIG. 7 is a chiral liquid chromatogram of product produced from acetophenone reduction catalyzed by an alcohol dehydrogenase mutant M12.
Figure 8:
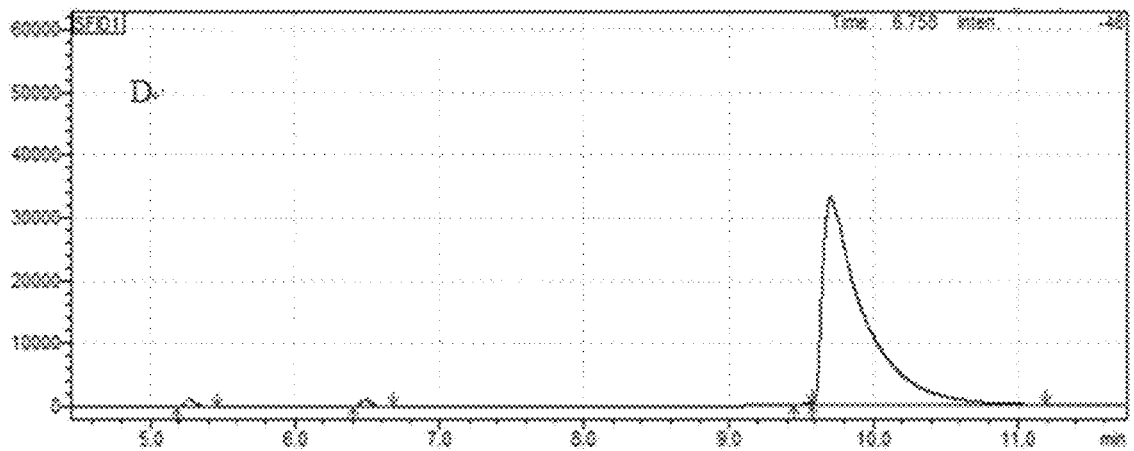
FIG. 8 is a chiral liquid chromatogram of product produced from 4'-Chloroacetophenon reduction catalyzed by an alcohol dehydrogenase mutant M11.
Figure 9:
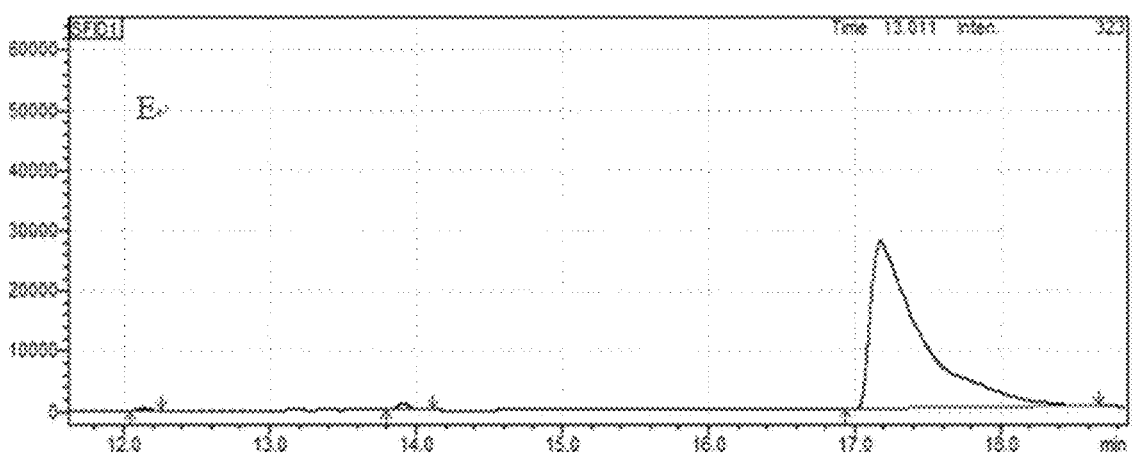
FIG. 9 is a chiral liquid chromatogram of product produced from 4-Chlorophenacyl Chloride reduction catalyzed by an alcohol dehydrogenase mutant M14.

The present disclosure will be described in detail below by means of specific embodiments, but this does not limit the present disclosure to the scope of the described embodiments. The experimental methods without indicated specific experimental conditions in the following embodiments may be selected according to conventional methods and conditions, or according to the specification.

Example 1: Method for Measuring Activity of Alcohol Dehydrogenase and Optical Purity of Product Adopting a total reaction system of 200 μL, including: 1.0 mM NADPH, 1.0 mM substrate CPMK and sodium phosphate buffer (PBS, 100 mM, pH 7.0), fully and evenly mixing, maintaining at 30° C. for 2 min, adding an appropriate amount of enzyme solution, and detecting the change in light absorption at 340 nm.

The enzyme activity was calculated by the following formula:

$$\text{Enzyme activity }(U) = EW \times V \times 10^3 / (6220 \times l);$$

in the formula, EW is the change in absorbance at 340 nm in 1 min; V is the volume of a reaction solution in mL; 6220 is the molar extinction coefficient of NADPH in L/mol·cm); and 1 is the optical path distance in cm. One activity unit (U) corresponds to the amount of enzyme required to catalyze the oxidation of 1 μmol NADPH per minute under the above conditions.

Method for determining optical purity ee:

$$ee = \frac{AS - AR}{AS + AR} \times 100\%;$$

As: molar concentration of (S)-CPMA obtained by liquid chromatography; and $A_R$: molar concentration of (R)-CPMA obtained by liquid chromatography.

Example 2: Construction of Alcohol Dehydrogenase Mutant Gene and Recombinant Expression Transformant A whole plasmid PCR method was used for site-directed mutagenesis on amino acid residues at positions 214 and 237 to construct an iterative combination mutant. The primer design was as Table 1 (all described in the 5'-3' direction, and the underline represents the mutation site):

TABLE 1

Site-directed mutagenesis primer design table

| Primer | Sequence |
|---|---|
| E214A-F | AGAAACTAAATGCAACTTGTG (SEQ ID No. 3) |
| E214A-R | TCACAAGTTGCATTTAGTTTC (SEQ ID No. 4) |
| E214T-F | AGAAACTAAATACCACTTGTG (SEQ ID No. 5) |
| E214T-R | TCACAAGTGGAATTTAGTTTC (SEQ ID No. 6) |
| E214R-F | AGAAACTAAATGCAACTTGTG (SEQ ID No. 7) |
| E214R-R | TCACAAGTTGCATTTAGTTTC (SEQ ID No. 8) |
| E214N-F | AGAAACTAAATAATACTTGTG (SEQ ID No. 9) |
| E214N-R | TCACAAGTATTATTTAGTTTC (SEQ ID No. 10) |
| E214D-F | AGAAACTAAATGATACTTGTG (SEQ ID No. 11) |
| E214D-R | TCACAAGTATCATTTAGTTTC (SEQ ID No. 12) |
| E214C-F | AGAAACTAAATTGTACTTGTG (SEQ ID No. 13) |
| E214C-R | TCACAAGTACAATTTAGTTTC (SEQ ID No. 14) |
| E214E-F | AGAAACTAAATGAAACTTGTG (SEQ ID No. 15) |
| E214E-R | TCACAAGTTTCATTTAGTTTC (SEQ ID No. 16) |
| E214Q-F | AGAAACTAAATCAGACTTGTG (SEQ ID No. 17) |
| E214Q-R | TCACAAGTCTGATTTAGTTTC (SEQ ID No. 18) |
| E214G-F | AGAAACTAAATGGTACTTGTG (SEQ ID No. 19) |
| E214G-R | TCACAAGTCCAATTTAGTTTC (SEQ ID No. 20) |
| E214H-F | AGAAACTAAATCATACTTGTG (SEQ ID No. 21) |
| E214H-R | TCACAAGTATGATTTAGTTTC (SEQ ID No. 22) |
| E214I-F | AGAAACTAAATATTACTTGTG (SEQ ID No. 23) |
| E214I-R | TCACAAGTAATATTTAGTTTC (SEQ ID No. 24) |
| E214L-F | AGAAACTAAATCTGACTTGTG (SEQ ID No. 25) |
| E214L-R | TCACAAGTCAGATTTAGTTTC (SEQ ID No. 26) |
| E214K-F | AGAAACTAAATAAACTTGTG (SEQ ID No. 27) |
| E214K-R | TCACAAGTTTTATTTAGTTTC (SEQ ID No. 28) |
| E214M-F | AGAAACTAAATATGACTTGTG (SEQ ID No. 29) |
| E214M-R | TCACAAGTCATATTTAGTTTC (SEQ ID No. 30) |
| E214F-F | AGAAACTAAATTTTACTTGTG (SEQ ID No. 31) |
| E214F-R | TCACAAGTAAAATTTAGTTTC (SEQ ID No. 32) |
| E214P-F | AGAAACTAAATCCGACTTGTG (SEQ ID No. 33) |
| E214P-R | TCACAAGTCGGATTTAGTTTC (SEQ ID No. 34) |
| E214W-F | AGAAACTAAATTGGACTTGTG (SEQ ID No. 35) |
| E214W-R | TCACAAGTCCTATTTAGTTTC (SEQ ID No. 36) |
| E214Y-F | AGAAACTAAATTATACTTGTG (SEQ ID No. 37) |
| E214Y-R | TCACAAGTATAATTTAGTTTC (SEQ ID No. 38) |
| E214V-F | AGAAACTAAATGTTACTTGTG (SEQ ID No. 39) |
| E214V-R | TCACAAGTAACATTTAGTTTC (SEQ ID No. 40) |
| S237A-F | ACTCACTTCGCACAATTCATT (SEQ ID No. 41) |
| S237A-R | AATGAATTGTGCGAAGTGAGT (SEQ ID No. 42) |
| S237C-F | ACTCACTTCTGTCAATTCATT (SEQ ID No. 43) |
| S237C-R | AATGAATTGACAGAAGTGAGT (SEQ ID No. 44) |

A PCR reaction system was: a PCR reaction system (50 μL) including KOD enzyme (2.5 U/mL) 1.0 μL, template (5-50 ng) 1.0 μL, dNTP 4.0 μL, 10× reaction buffer 5.0 μL, forward primer 1.0 µL, reverse primer 1.0 µL, and the rest of ddH2O to make the reaction system 50 µL in total.

A PCR amplification procedure was: (1) denaturation at 94° C. for 3 min, (2) denaturation at 94° C. for 30 sec, (3) annealing at 54° C. for 30 sec, (4) extension at 72° C. for 150 sec, repeating steps (2) to (4) for 10-15 cycles, finally extension at 72° C. for 10 min, and storing a PCR amplification product at 4° C.

After PCR, DpnI restriction enzyme was added into a reaction mixture and incubated at 37° C. for 1 h, 10 µL digested PCR reaction solution was transferred into 50 µL *E. coli* BL21 (DE3) competent cells through $CaCl_2$ thermal transformation, and the cells were used to uniformly coat an LB agar plate containing 50 µg/mL kanamycin sulfate for inversion culture at 37° C. for 12 h.

Example 3: Expression and Purification of Alcohol Dehydrogenase and Mutant Thereof Recombinant *Escherichia coli* carrying a stereoselective improvement mutant was inoculated into an LB medium containing kanamycin sulfate (50 µg/mL) at a transfer amount of 2% for shake cultivation at 37° C. and 200 rpm, 0.2 mM isopropyl-β-D-thiogalactofuranoside (IPTG) was added for induction at 25° C. when the absorbance $OD_{600}$ of the medium reached 0.8, after 8 hours of induction, a strain for efficient expression of a recombinant alcohol dehydrogenase mutant was obtained through 10 minutes of centrifugation at 8000 rpm, and the collected cells was suspended in a potassium phosphate buffer (100 mM, pH 6.0) for ultrasonication.

A column used for purification was a nickel affinity column HisTrap FF crude, and purification was achieved through affinity chromatography using a histidine tag on recombinant protein. The nickel column was equilibrated with a solution A first, a crude enzyme solution was loaded, a penetrating peak was further eluted off using the solution A, and after equilibrium, a solution B (20 mM sodium phosphate, 500 mM NaCl, and 1000 mM imidazole, pH 7.4) was used for gradient elution to elute off the recombinant protein bound to the nickel column, so as to obtain the recombinant alcohol dehydrogenase mutant. The purified protein was subjected to activity measurement (CPMK as substrate, and NADPH as coenzyme) and SDS-PAGE analysis. After purification of the nickel column, a single band was displayed at around 45 kDa, and the amount of impure protein was small, indicating that the column purification effect was good. The purified alcohol dehydrogenase protein was then replaced into a Tris-HCl (100 mM, pH 7.0) buffer using a Hi Trap Desalting column (GE Healthcare).

Example 4: Kinetic and Stereoselective Analysis of Alcohol Dehydrogenase Mutant The activity of KpADH at different substrate concentrations and coenzyme concentrations was determined, and a double reciprocal curve was made based on the reciprocal of activity and substrate concentration to calculate kinetic parameters.

Two mutants of S237A and S237C valuable for modification of asymmetric synthesis R- and S- are obtained by random mutation screening, and the two sites are used as templates for random mutation. The characterization results of the mutant strains are shown in Table 2: the mutant E214V/S237A asymmetrically reduces a substrate to obtain (R)-CPMA, and the e.e. value reaches 98.5%; the mutant E214G/S237C asymmetrically reduces a substrate to obtain (S)-CPMA, which achieves stereoselective inversion, and the e.e. value is 75.5%. The stereoselectivity of other mutants does not improve much compared with WT. It can be known by combining the data in Tables 2 and 3 that the 214 site of alcohol dehydrogenase is a site that is important for determining selectivity improvement and inversion.

TABLE 2

Kinetic parameters and stereoselectivity of alcohol dehydrogenase random mutants

| Enzyme | $K_m$ [mM] | $V_{max}$ [uM/min · mg] | $K_{cat}$ [$s^{-1}$] | $K_{cat}/K_m$ [$mM^{-1} \cdot s^{-1}$] | e.e. |
|---|---|---|---|---|---|
| WT | 0.76 ± 0.19 | 21.29 ± 2.14 | 14.19 ± 1.16 | 18.68 ± 0.62 | 81.7 (R) |
| S237C | 1.01 ± 0.10 | 20.91 ± 1.82 | 13.94 ± 0.99 | 13.8 ± 0.25 | 27 (R) |
| S237A | 0.58 ± 0.03 | 36.52 ± 3.02 | 24.35 ± 1.26 | 41.98 ± 2.36 | 96.1 (R) |
| F320W/S237A | 1.66 ± 0.02 | 16.6 ± 0.37 | 11.07 ± 0.25 | 6.66 ± 0.42 | 76.3 (R) |
| F320V/S237A | 1.15 ± 0.05 | 8.9 ± 0.78 | 5.9 ± 0.09 | 5.15 ± 0.69 | 84.4 (R) |
| E214G/S237C | 0.31 ± 0.02 | 9.54 ± 0.16 | 6.30 ± 0.11 | 22.10 ± 1.37 | 75.5 (S) |
| H249Y/S237C | 0.98 ± 0.02 | 16.5 ± 0.56 | 11.0 ± 0.83 | 11.22 ± 0.98 | 69.5 (R) |
| L60F/S237C | 1.12 ± 0.02 | 12.6 ± 0.49 | 8.40 ± 0.23 | 7.50 ± 0.69 | 79.6 (R) |
| A269C/S237C | 1.56 ± 0.02 | 22.6 ± 0.59 | 15.4 ± 0.86 | 9.90 ± 0.36 | 66.9 (R) |
| N220G/S237C | 0.72 ± 0.02 | 20.6 ± 0.44 | 13.73 ± 0.16 | 19.07 ± 1.06 | 33.9 (R) |
| E214V/S237A | 0.32 ± 0.03 | 12.69 ± 0.40 | 8.46 ± 0.27 | 26.54 ± 1.66 | 98.5 (R) |

The E214 site adopts a site-directed mutagenesis strategy to replace glutamic acid with other 19 amino acids. The characterization results of the constructed new mutants are shown in Table 3 below, the $K_m$ of KpADH is 0.76 $mM^{-1}$, the configuration of a reduction product is R configuration, the ee value is 81.7%, and the $K_m$ of only E214G, E214V and E214I in the mutants is significantly reduced, to 0.25 mM, 0.42 mM and 0.41 mM, respectively. The stereoselectivity of the mutants E214Y, E214V, E214I and E214F in asymmetric synthesis of (R)-CPMA is significantly improved, to 93.8%, 95.3%, 93.0% and 91.9%, respectively; the mutants E214G, E214Q, E214S, E214N and E214R show significantly reduced stereoselectivity, among which the asymmetric reduction of E214G produces (S)-CPMA, the e.e. value is 25.6 (S), and the other four mutant strains still synthesize (R)-CPMA, which are 58.5%, 14.2%, 58.1% and 42.5%, respectively.

TABLE 3

Kinetic parameters and stereoselectivity of a single-site mutant of alcohol dehydrogenase mutant E214

| Enzyme | $K_m$ [mM] | $V_{max}$ uM/min · mg | $K_{cat}$ [s$^{-1}$] | $K_{cat}/K_m$ [mM$^{-1}$ · s$^{-1}$] | ee % |
|---|---|---|---|---|---|
| WT | 0.76 ± 0.19 | 21.29 ± 2.14 | 14.19 ± 1.16 | 18.68 ± 0.62 | 81.7 (R) |
| E214Y | 0.69 ± 0.07 | 17.69 ± 0.81 | 11.79 ± 0.44 | 17.09 ± 0.94 | 93.8 (R) |
| E214W | 1.19 ± 0.19 | 14.34 ± 1.65 | 9.56 ± 0.90 | 8.03 ± 1.21 | 82.5 (R) |
| E214V | 0.42 ± 0.08 | 13.36 ± 0.89 | 8.91 ± 0.48 | 21.21 ± 0.72 | 95.3 (R) |
| E214T | 0.75 ± 0.13 | 30.62 ± 2.05 | 20.41 ± 1.11 | 27.22 ± 0.41 | 72.8 (R) |
| E214S | 0.54 ± 0.07 | 17.79 ± 0.88 | 11.86 ± 0.48 | 21.96 ± 0.68 | 14.2 (R) |
| E214R | 0.98 ± 0.08 | 23.77 ± 0.90 | 15.85 ± 0.49 | 16.17 ± 2.17 | 42.5 (R) |
| E214P | 0.88 ± 0.15 | 19.02 ± 1.34 | 12.68 ± 0.72 | 14.41 ± 1.12 | 68.2 (R) |
| E214N | 0.42 ± 0.06 | 34.35 ± 2.05 | 22.90 ± 1.12 | 54.52 ± 2.17 | 58.1 (R) |
| E214M | 0.73 ± 0.08 | 38.80 ± 1.84 | 25.87 ± 1.00 | 35.43 ± 1.12 | 83.8 (R) |
| E214L | 0.52 ± 0.07 | 16.74 ± 0.88 | 11.16 ± 0.48 | 21.46 ± 0.75 | 78.1 (R) |
| E214K | 0.79 ± 0.19 | 23.22 ± 2.21 | 15.48 ± 1.20 | 19.59 ± 1.24 | 62.6 (R) |
| E214I | 0.41 ± 0.04 | 13.15 ± 0.43 | 8.77 ± 0.23 | 21.38 ± 0.47 | 93.0 (R) |
| E214F | 0.51 ± 0.06 | 23.38 ± 0.93 | 15.59 ± 0.51 | 30.56 ± 0.81 | 91.9 (R) |
| E214D | 0.55 ± 0.06 | 15.89 ± 0.75 | 10.59 ± 0.41 | 19.26 ± 0.61 | 63.8 (R) |
| E214C | 0.77 ± 0.11 | 18.37 ± 1.17 | 12.25 ± 0.64 | 15.90 ± 0.68 | 78.9 (R) |
| E214A | 0.81 ± 0.13 | 13.37 ± 0.88 | 8.91 ± 0.48 | 11.00 ± 0.48 | 76.3 (R) |
| E214Q | 1.3 ± 0.20 | 24.4 ± 0.20 | 16.26 ± 1.33 | 12.61 ± 0.93 | 58.5 (R) |
| E214G | 0.25 ± 0.15 | 8.26 ± 0.15 | 5.5 ± 0.10 | 22.10 ± 1.34 | 25.6 (S) |
| E214H | 0.75 ± 0.52 | 12.6 ± 1.56 | 8.4 ± 2.22 | 11.2 ± 1.58 | 77.5 (R) |

In order to improve the R- and S-stereoselectivity of the enzyme, E214V, E214Y and E214I are used as templates to replace serine at site 237 with glycine, and E214G, E214Q, E214S, E214N and E214R are used as templates to replace serine at site 237 with cysteine. The characterization results of the constructed new mutants are shown in Table 4 below: Kcat/Km of mutant enzymes E214V/S237A, E214Y/S237A and E214I/S237A is slightly higher than WT, but the stereoselectivity in asymmetric synthesis of (R)-CPMA is significantly improved, to 98.5%, 99.1% and 98.3%, respectively; the products synthesized by E214G/S237C, E214Q/S237C, E214S/S237C, E214N/S237C and E214R/S237C are all (S)-CPMA, among which E214G/S237C has the highest selectivity, reaching 75.5% (S), and the catalytic efficiency Kcat/Km is slightly improved compared with WT. The above combined mutants have high guiding value for studying modification of asymmetric synthesis of R- and S- by the enzyme.

TABLE 4

Kinetic parameters and stereoselectivity of alcohol dehydrogenase combined mutants

| Enzyme | $K_m$ [mM] | $V_{max}$ [uM/min · mg] | $K_{cat}$ [s$^{-1}$] | $K_{cat}/K_m$ [mM$^{-1}$ · s$^{-1}$] | e.e. |
|---|---|---|---|---|---|
| WT | 0.76 ± 0.19 | 21.29 ± 2.14 | 14.19 ± 1.16 | 18.68 ± 0.62 | 81.7 (R) |
| E214V/S237A | 0.32 ± 0.03 | 12.69 ± 0.40 | 8.46 ± 0.27 | 26.54 ± 1.66 | 98.5 (R) |
| E214Y/S237A | 0.62 ± 0.02 | 23.70 ± 0.37 | 15.80 ± 0.25 | 25.49 ± 0.42 | 99.1 (R) |
| E214I/S237A | 0.47 ± 0.05 | 18.09 ± 0.78 | 12.06 ± 0.52 | 25.78 ± 1.65 | 98.3 (R) |
| E214G/S237C | 0.31 ± 0.02 | 9.54 ± 0.16 | 6.30 ± 0.11 | 22.10 ± 1.37 | 75.5 (S) |
| E214Q/S237C | 0.55 ± 0.02 | 10.59 ± 0.16 | 7.06 ± 0.63 | 12.84 ± 1.44 | 44.6 (S) |
| E214S/S237C | 0.40 ± 0.02 | 12.5 ± 0.16 | 8.33 ± 0.17 | 20.8 ± 1.97 | 52.0 (S) |
| E214N/S237C | 0.22 ± 0.02 | 8.80 ± 0.20 | 5.87 ± 0.13 | 26.78 ± 1.84 | 43.6 (S) |
| E214R/S237C | 0.88 ± 0.02 | 15.6 ± 0.16 | 10.4 ± 0.11 | 11.8 ± 1.37 | 48.3 (S) |

Example 5: Substrate Specificity Analysis of Alcohol Dehydrogenase Mutant

The reduction on prochiral carbonyl compounds by the alcohol dehydrogenase mutants obtained in Example 3 was studied. The pro-chiral carbonyl compounds include (4-chlorophenyl)-(pyridin-2-yl)-methanone (CPMK), phenyl-(pyridin-2-yl)-methanone, (4-chlorophenyl)-(phenyl)-methanone, (4-bromophenyl)(phenyl)methanone, (4-fluorophenyl)(phenyl)methanone, (4-methoxyphenyl)-(phenyl)-methanone, (4-nitrophenyl)(phenyl)methanone, 1-(pyridin-2-yl)ethanone, acetophenone, 4'-Chloroacetophenone, 4-chlorophenacyl chloride, ethyl 2-oxo-4-phenylbutanoate (OPBE), ethyl 4-chloro-3-oxobutanoate, and methyl 2-oxo-2-phenylacetate.

As can be seen from Table 5, the alcohol dehydrogenase exhibited high activity toward ester substrates, such as ethyl 2-oxo-4-phenylbutanoate, ethyl 4-chloro-3-oxobutanoate and methyl 2-oxo-2-phenylacetate. WT exhibited the highest activity of 41.84 U/mg toward ethyl 4-chloro-3-oxobutanoate, which suggested that the substituted chlorine atom is critical for the activity increasing of enzyme. E214I/S237A exhibited the highest activity of 30.09 U/mg toward 4-chlorophenacyl chloride while the lowest activity toward acetophenone and 1-(pyridin-2-yl)ethanone.

TABLE 5

Substrate specificity (specific activity, U/mg) of alcohol dehydrogenase mutants

| Substrate | WT | E214V/S237A | E214I/S237A | E214Y/S237A | E214G/S237C | E214Q/S237C | E214S/S237C | E214R/S237C | E214N/S237C |
|---|---|---|---|---|---|---|---|---|---|
| acetophenone | 0.99 | 0.16 | 0.09 | 0.26 | 0.15 | 0.22 | 0.19 | 0.26 | 0.84 |
| 1-(pyridin-2-yl)ethanone | 1.34 | 0.12 | 0.08 | 0.25 | 0.07 | 0.12 | 0.09 | 0.18 | 0.52 |
| 4'-chloroacetophenone | 4.15 | 2.37 | 1.42 | 2.25 | 0.12 | 0.09 | 0.25 | 0.36 | 0.32 |
| phenyl-(pyridin-2-yl)-methanone | 4.07 | 2.86 | 2.94 | 4.06 | 3.10 | 5.65 | 5.69 | 4.21 | 7.50 |
| CPMK | 12.09 | 9.21 | 12.38 | 14.48 | 4.84 | 3.65 | 2.55 | 1.96 | 7.48 |
| 4-chlorophenacyl chloride | 20.67 | 27.07 | 30.09 | 25.70 | 9.81 | 10.25 | 5.96 | 6.69 | 10.02 |
| OPBE | 27.02 | 24.47 | 21.73 | 22.02 | 10.26 | 9.89 | 15.58 | 22.48 | 17.10 |

TABLE 5-continued

Substrate specificity (specific activity, U/mg) of alcohol dehydrogenase mutants

| | WT | E214V/ S237A | E214I/ S237A | E214Y/ S237A | E214G/ S237C | E214Q/ S237C | E214S/ S237C | E214R/ S237C | E214N/ S237C |
|---|---|---|---|---|---|---|---|---|---|
| Ph-C(O)-COOMe | 39.77 | 27.64 | 30.28 | 22.61 | 21.25 | 22.65 | 30.69 | 30.69 | 13.21 |
| Cl-CH₂-C(O)-CH₂-C(O)-OEt | 41.84 | 8.03 | 5.58 | 7.74 | 1.55 | 2.65 | 1.59 | 1.88 | 5.80 |

It can be seen from Table 6 that mutants E214G/S237C, E214Q/S237C, E214S/S237C, E214N/S237C and E214R/S237C all exhibited high stereoselecticity toward the acetophenone to obtain R configuration products and the mutant E214G/S237C displayed the highest ee value of 99.5%. Substrate 4-chloroacetophenone was reduced by E214I/S237A with 99.4% ee (R), while substrate 4-chlorobenzoyl chloride was reduced by E214S/S237C with the highest ee value of 99.6%. (4-bromophenyl)-(phenyl)-methanone and p-nitrobenzophenone were reduced by E214N/S237A with 98.5% ee (S) and 99.2% ee (S), respectively. Substrate p-nitrobenzophenone was reduced by E214N/S237C with 99.1% ee (S). All the products above were recrystallized from ethyl acetate and gave more than 99.9% optical purity.

TABLE 6

Stereoselectivity of alcohol dehydrogenase mutants on different substrates

| | WT | E214/ S237A | E214I/ S237A | E214Y/ S237A | E214G/ S237C | E214Q/ S237C | E214S/ S237C | E214R/ S237C | E214N/ S237C |
|---|---|---|---|---|---|---|---|---|---|
| acetophenone | 88.6 (R) | 17.1 (R) | 9.69 (R) | 32.1 (R) | 99.5 (R) | 96.5 (R) | 98.9 (R) | 98.3 (R) | 99.0 (R) |
| 4-chloroacetophenone | 92.9 (R) | 97.8 (R) | 99.4 (R) | 97.9 (R) | 93.8 (R) | 93.5 (R) | 95.6 (R) | 97.2 (R) | 97.4 (R) |
| 2-chloro-1-(4-chlorophenyl)ethanone | 95.2 (R) | 75.2 (R) | 76.4 (R) | 61.6 (R) | 96.2 (R) | 97.6 (R) | 99.6 (R) | 92.9 (R) | 93.6 (R) |
| phenyl(pyridin-2-yl)methanone | 27.5 (R) | 36.6 (R) | 36.8 (R) | 18.2 (R) | 51.9 (R) | 56.6 (R) | 52.6 (R) | 50.1 (R) | 51.5 (R) |
| (4-chlorophenyl)(pyridin-2-yl)methanone | 83.7 (R) | 98.7 (R) | 98.4 (R) | 99.1 (R) | 43.2 (S) | 44.6 (S) | 52.0 (S) | 48.3 (S) | 57.1 (S) |

TABLE 6-continued

Stereoselectivity of alcohol dehydrogenase mutants on different substrates

| | WT | E214/ S237A | E214I/ S237A | E214Y/ S237A | E214G/ S237C | E214Q/ S237C | E214S/ S237C | E214R/ S237C | E214N/ S237C |
|---|---|---|---|---|---|---|---|---|---|
| 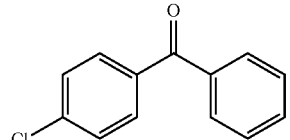 | 52.4 (S) | 54.2 (S) | 52.6 (S) | 89.3 (S) | 86.2 (R) | 88.6 (R) | 88.1 (R) | 49.8 (R) | 57.1 (R) |
| 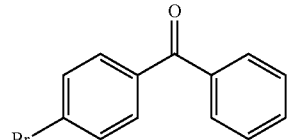 | 70.5 (S) | 88.1 (S) | 93.4 (S) | 98.5 (S) | 91.4 (R) | 92.6 (R) | 90.6 (R) | 89.9 (R) | 91.9 (R) |
| 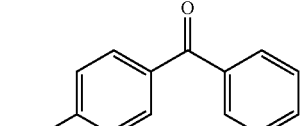 | 37.6 (R) | 85.3 (S) | 86.5 (S) | 99.2 (S) | 93.3 (R) | 93.3 (R) | 91.9 (R) | 88.0 (R) | 90.7 (R) |
| 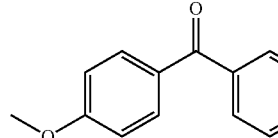 | 27.3 (R) | 81.8 (S) | 81.8 (S) | 79.3 (S) | 93.8 (S) | 90.6 (R) | 92.3 (R) | 91.9 (R) | 99.1 (S) |

Example 6: Preparation of (R)-CPMA Through Asymmetric Reduction of CPMK by Alcohol Dehydrogenase Mutants A 20 mL biocatalytic system is established: 100 mM of potassium phosphate buffer (pH 7.0) is used, the mutant E214Y/S237A obtained in Example 2 and wild KpADH 10 g/L are added, and 100 mM, 200 mM and 500 mM of CPMK are added (substrates are added in batches). The other 8 reactions are established in the same manner as follows: mutant E214G/S237C was applied as biocatalyst while acetophenone was used as the substrate; mutant E214I/S237A was applied as biocatalyst while (4-chlorophenyl)-(phenyl)-methanone was used as the substrate; mutant E214G/S237C was applied as biocatalyst while 4-chlorobenzoyl chloride was used as the substrate; mutant E214Y/S237A was applied as biocatalyst while (4-bromophenyl)-(phenyl)-methanone was used as the substrate; mutant E214N/S237C was applied as biocatalyst while (4-methoxyphenyl)-(phenyl)-methanone was used as the substrate; All the reactions are carried out at 30° C. and 200 rpm for 12 h with a constant pH of 7.5. The conversion results are shown in Tables 7 to 11. WT KpADH displayed 82% ee in the asymmetric synthesis of (R)-CPMA while E214Y/S237A exhibited increased ee of 99.1%. The pure (R)-CPMA were recrystallized from ethyl acetate at 4° C. and gave 99.9% optical purity. In the asymmetric reduction catalyzed by E214I/S237A, E214G/S237C and E214S/S237C, the optical purity of corresponding products were all reached 99.9% after recrystallization. By contrast, only 20 mM p-nitrobenzophenone could be afforded in the asymmetric reduction catalyzed by E214Y/S237A due to the poor solubility of substrate and low tolerance of the enzyme. Besides, the conversion cannot reach 100% with 24 h in the asymmetric reduction of (4-bromophenyl)-(phenyl)-methanone and p-nitrobenzophenone due to the low enzyme activity.

TABLE 7

Asymmetric reduction of CPMK catalyzed by wild-type alcohol dehydrogenase KpADH

| | Conversion rate (%) | | |
|---|---|---|---|
| Reaction time (h) | 100 mM | 200 mM | 500 mM |
| 1 | 50.5 | 35.6 | 22.5 |
| 2 | 65.5 | 46.9 | 30 |
| 3 | 79.5 | 62.0 | 55.6 |
| 4 | 88.8 | 75.5 | 66.5 |
| 6 | 98.5 | 95.6 | 80.2 |
| 8 | >99.9 | 98.8 | 93.2 |
| 12 | >99.9 | 99.4 | 95.6 |
| 24 | >99.9 | 99.7 | 99.2 |

TABLE 8

Asymmetric reduction of CPMK catalyzed by alcohol dehydrogenase mutant E214Y/S237A

| | Conversion rate (%) | | |
|---|---|---|---|
| Reaction time (h) | 100 mM | 200 mM | 500 mM |
| 1 | 66 | 45.5 | 25.5 |
| 2 | 80 | 65.5 | 33.5 |
| 3 | 89.5 | 75.9 | 45.8 |
| 4 | 94 | 88.8 | 59.9 |
| 6 | 96.6 | 95.6 | 77.9 |
| 8 | 99.5 | 99.1 | 90.2 |

TABLE 8-continued

Asymmetric reduction of CPMK catalyzed by alcohol dehydrogenase mutant E214Y/S237A

| Reaction time (h) | Conversion rate (%) | | |
|---|---|---|---|
| | 100 mM | 200 mM | 500 mM |
| 12 | >99.9 | 99.7 | 95.7 |
| 24 | >99.9 | >99.9 | 99.5 |

TABLE 9

Asymmetric reduction of acetophenone catalyzed by alcohol dehydrogenase mutant E214G/S237C

| Reaction time (h) | Conversion rate (%) | | |
|---|---|---|---|
| | 100 mM | 200 mM | 500 mM |
| 1 | 42 | 35 | 20.9 |
| 2 | 53 | 49 | 34.5 |
| 3 | 65 | 60 | 49.6 |
| 4 | 77 | 72 | 62.6 |
| 6 | 95 | 85.9 | 77.9 |
| 8 | 99.0 | 93.6 | 88.6 |
| 12 | >99.9 | 99.2 | 92.9 |
| 24 | >99.9 | 99.7 | 99.2 |

TABLE 10

Asymmetric reduction of 4-chlorobenzoyl chloride catalyzed by alcohol dehydrogenase mutant E214S/S237C

| Reaction time (h) | Conversion rate (%) | | |
|---|---|---|---|
| | 100 mM | 200 mM | 500 mM |
| 1 | 66 | 55 | 35.6 |
| 2 | 79 | 69 | 49.6 |
| 3 | 90 | 76 | 66.4 |
| 4 | 98 | 85.9 | 79.3 |
| 6 | 99.2 | 96.4 | 89.0 |
| 8 | 99.8 | 99.1 | 95.6 |
| 12 | >99.9 | 99.8 | 96.9 |
| 24 | >99.9 | >99.9 | 98.9 |

TABLE 11

Asymmetric reduction of 4-chloroacetophenone catalyzed by alcohol dehydrogenase mutant E214I/S237A

| Reaction time (h) | Conversion rate (%) | | |
|---|---|---|---|
| | 100 mM | 200 mM | 500 mM |
| 1 | 59 | 40 | 28.5 |
| 2 | 72 | 52.4 | 38.9 |
| 3 | 89 | 69.5 | 50.0 |
| 4 | 85 | 76.9 | 64.2 |
| 6 | 97.6 | 88.6 | 80.9 |
| 8 | 99.8 | 95.6 | 90.2 |
| 12 | >99.9 | 99.2 | 94.9 |
| 24 | >99.9 | 99.7 | 99.2 |

TABLE 12

Asymmetric reduction of 4-nitroacetophenone catalyzed by alcohol dehydrogenase mutant E214Y/S237A

| Reaction time (h) | Conversion rate (%) | | |
|---|---|---|---|
| | 10 mM | 20 mM | 50 mM |
| 1 | 32 | 22 | 10.5 |
| 2 | 48 | 35.5 | 22.5 |
| 3 | 60 | 55.8 | 35.9 |
| 4 | 85 | 69.5 | 49.5 |
| 6 | 95 | 90.4 | 60.9 |
| 8 | 99.8 | 95.6 | 82.6 |
| 12 | >99.9 | 99.2 | 85.5 |
| 24 | >99.9 | 99.5 | 86.5 |

The alcohol dehydrogenase mutants of the present invention not only have very good performance in high-efficiency, high-stereoselectivity asymmetric reduction of CPMK, but also have higher catalytic efficiency and high stereoselectivity on other aryl ketone substrates.

What is claimed is:

1. An alcohol dehydrogenase mutant, wherein the alcohol dehydrogenase mutant comprises an amino acid sequence having all of SEQ ID NO:2 except for:
- a substitution of valine for glutamate at position 214 of the amino acid sequence SEQ ID NO: 2;
- a substitution of tyrosine for glutamate at position 214 of the amino acid sequence SEQ ID NO: 2;
- a substitution of isoleucine for glutamate at position 214 of the amino acid sequence SEQ ID NO: 2;
- a substitution of glutamine for glutamate at position 214 of the amino acid sequence SEQ ID NO: 2;
- a substitution of serine for glutamate at position 214 of the amino acid sequence SEQ ID NO: 2;
- a substitution of asparagine for glutamate at position 214 of the amino acid sequence SEQ ID NO: 2;
- a substitution of arginine for glutamate at position 214 of the amino acid sequence SEQ ID NO: 2;
- a substitution of valine for glutamate at position 214 of the amino acid sequence SEQ ID NO: 2, and the substitution of alanine for serine at position 237;
- a substitution of tyrosine for glutamate at position 214 of the amino acid sequence SEQ ID NO: 2, and the substitution of alanine for serine at position 237;
- a substitution of isoleucine for glutamate at position 214 of the amino acid sequence SEQ ID NO: 2, and the substitution of alanine for serine at position 237;
- a substitution of glycine for glutamate at position 214 of the amino acid sequence SEQ ID NO: 2, and the substitution of cysteine for serine at position 237;
- a substitution of glutamine for glutamate at position 214 of the amino acid sequence SEQ ID NO: 2, and the substitution of cysteine for serine at position 237;
- a substitution of serine for glutamate at position 214 of the amino acid sequence SEQ ID NO: 2, and the substitution of cysteine for serine at position 237;

a substitution of asparagine for glutamate at position 214 of the amino acid sequence SEQ ID NO: 2, and the substitution of cysteine for serine at position 237; and a substitution of arginine for glutamate at position 214 of the amino acid sequence SEQ ID NO: 2, and the substitution of cysteine for serine at position 237, and wherein the alcohol dehydrogenase mutant has alcohol dehydrogenase activity.

2. A method for producing chiral (4-chlorophenyl)-(pyridin-2-yl)-methanol (CPMA), which comprises:

combining the alcohol dehydrogenase mutant of claim 1 at a concentration of 1 to 10 kU/L with prochiral (4-chlorophenyl)-(pyridin-2-yl)-methanone (CPMK) at a concentration of 10 to 500 mM, and NADP+at a concentration of 0.1 to 1.0 mM;

adding a coenzyme circulation system comprising glucose dehydrogenase at a concentration of 1 to 10 kU/L, D-glucose at a concentration of 20 to 1000 mM, and a phosphate buffer;

incubating the coenzyme circulation system with the alcohol dehydrogenase mutant, CPMK, and NADP+at 30 to 35° C. and a pH of 6 to 8 for 1 to 24 hours to produce CPMA; and extracting the CPMA by adding an organic solvent after an asymmetric reduction reaction;

wherein the coenzyme circulation system further comprises: (i) phosphite and phosphite dehydrogenase (FTDH), (ii) formic acid and formate dehydrogenase (FDH), (iii) lactic acid and lactate dehydrogenase (LDH), or (iv) glycerol and glycerol dehydrogenase.

* * * * *